United States Patent [19]
Grane

[11] 4,319,570
[45] Mar. 16, 1982

[54] TRACHEAL SUCTION PUMP DESIGNED PRIMARILY FOR ASPIRATION PURPOSES
[75] Inventor: Christian Grane, Kokedal, Denmark
[73] Assignee: Ruth Lea Hesse, Rungsted Kyst, Denmark
[21] Appl. No.: 230,101
[22] Filed: Jan. 29, 1981

Related U.S. Application Data

[63] Continuation of Ser. No. 851,282, Nov. 14, 1977, abandoned.

[30] Foreign Application Priority Data

Nov. 12, 1976 [GB] United Kingdom ............... 47335/76

[51] Int. Cl.³ ............................................. A61M 1/00
[52] U.S. Cl. .................................... 128/278; 417/395
[58] Field of Search ............... 417/329, 395, 374, 402, 417/903, 394; 128/276, 278, 277, 297

[56] References Cited

U.S. PATENT DOCUMENTS

3,084,691  4/1963  Stoner ................................. 128/278
3,429,274  2/1969  Nilsson ............................... 417/395
3,749,527  7/1973  Slagle ................................. 417/402

Primary Examiner—Robert W. Michell
Assistant Examiner—J. L. Kruter
Attorney, Agent, or Firm—Spencer & Kaye

[57] ABSTRACT

A portable suction pump for life-saving purposes and normally driven by compressed gas. The pump includes a pump assembly having a suction chamber with an outlet leading to the ambient atmosphere and an inlet communicating with a secretion-receiving reservoir with attached tubing permitting suction of secretion, primarily from the air ducts of an unconscious patient. The pump is characterized by the pump assembly having a housing enclosing the suction chamber and closed at one end by a first annular diaphragm and, centrally sealingly attached thereto, a rigid body guided for movement relative to the housing and having wall portions defining, together with part of the housing, a motor chamber delimited from the suction chamber by a second annular diaphragm. The motor chamber communicates with a driving gas supply and exhaust connections and a valve arrangement for the intake and exhaust of compressed driving gas.

12 Claims, 6 Drawing Figures

Fig. 6

TRACHEAL SUCTION PUMP DESIGNED PRIMARILY FOR ASPIRATION PURPOSES

This application is a continuation of Applicant's co-pending U.S. application Ser. No. 851,282 filed Nov. 14, 1977, now abandoned.

Tracheal suction pumps are used to remove mucus, blood, vomit etc from the mouth, throat and air-ducts of an unconscious person.

The invention is specifically concerned with a category of tracheal suction pumps intended to be used at the scene of an accident and during transport of victims from the location to hospital. Pumps of this type must have either a built-in energy source, be manually operable or be driven by compressed driving gas, ie oxygen, which is normally taken to the scene of an accident for treating patients requiring artifical respiration.

Suction pumps with a built-in energy source, such as an electric battery or aerosol container, are subject to the disadvantage of requiring regular service to ensure that there is sufficient energy available when the pump is put into use. It is also characteristic for known products of this type that low temperatures greately diminish their performance.

Manually operated pumps have the advantage of being completely independent of energy sources, but, on the other hand, are more awkward to operate than automatically driven pumps.

Oxygen-driven pumps which are available on the market are all designed as ejector pumps where the driving gas is the active medium in the ejector and the sucked-in air is the passive medium. The ejector principle has the benefit of being very simply designed but the disadvantage that its efficiency is very limited. Consequently, tracheal ejector pumps which fulfil the requirements in respect to suction capacity use large amounts of driving gas and this is inconvenient as there is a limit to the amount of driving gas which can be transported to the scene of an accident.

It is the purpose of the invention to eliminate the above disadvantages and to provide a portable suction pump for lifesaving purposes and normally driven by compressed gas, said pump comprising a pump assembly having a suction chamber with an outlet leading to the ambient atmosphere and an inlet communicating with a secretion-receiving reservoir with attached tubing permitting suction of secretion, primarily from the air ducts of an unconscious patient. In accordance with the present invention such a pump is characterized by the pump assembly comprising a housing enclosing the suction chamber and closed at one end by means comprising a first annular diaphragm and, centrally sealingly attached thereto, a rigid body guided by means connected to said housing for movement relative to the housing and having wall portions defining, together with means forming part of the housing, a motor chamber delimited from said suction chamber by a second annular diaphragm, said motor chamber communicating with driving gas supply and exhaust connections and a valve arrangement for the intake and exhaust of compressed driving gas.

While this pump is operated by compressed driving gas, it is approximately four times as effective as ejector pumps. Also, should there be insufficient driving gas available, the pump, in accordance with a further aspect of the invention, may be manually operated fully as effectively as with compressed driving gas.

Over and above these advantages the pump of the invention has a compact, robust design and is not sensitive to changes in temperature.

Further features of the invention appear from the subclaims.

A presently preferred embodiment of the pump of the invention will be described hereafter by way of example and by reference to the drawings in which.

Figure 1:
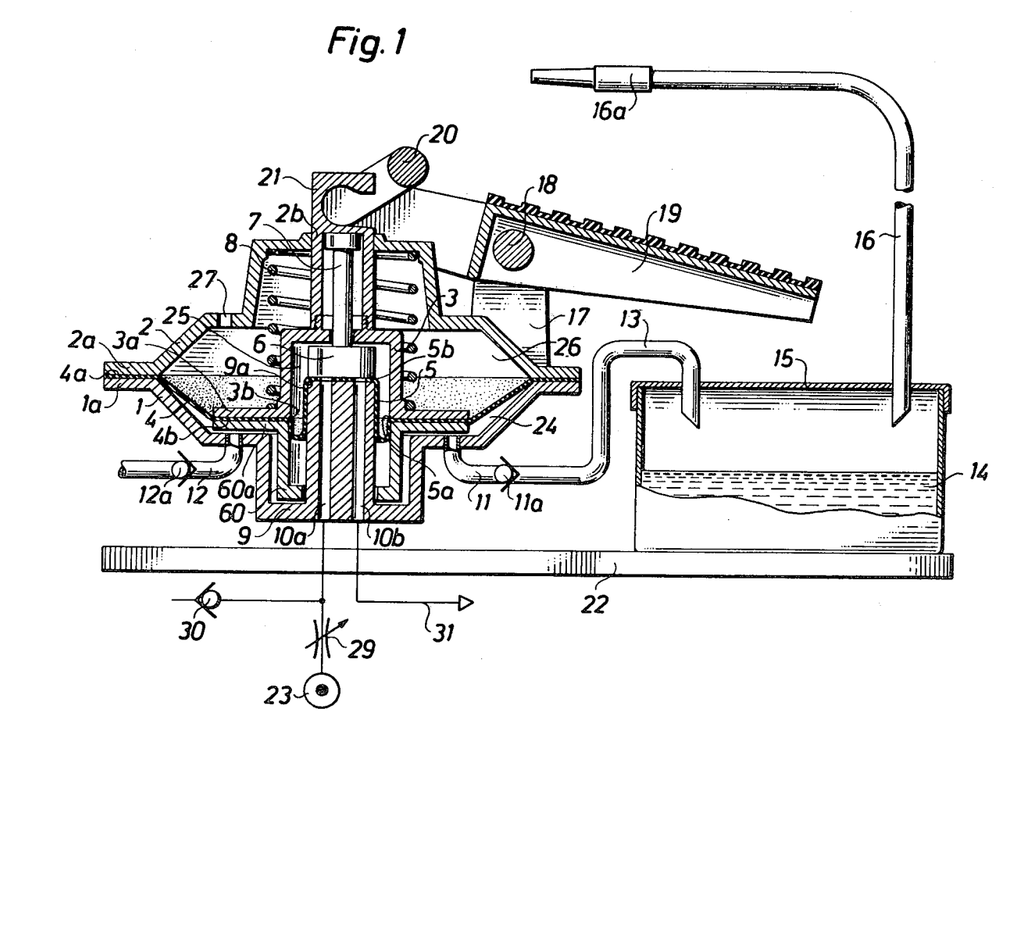
FIG. 1 is a schematic vertical section of the pump with the movable motor member in bottom position.

According to FIG. 1 the pump assembly consists of a stationary housing 1 which together with wall portions of a movable rigid body 3, a first annular flexible diaphragm 4 and a second annular flexible diaphragm 5 defines a central motor chamber 25 and a concentric pump chamber 24. Both diaphragms 4 and 5 are conveniently made of rubber. While the first diaphragm 4 is of the tapered type, the second diaphragm 5 is of the rolling type. A cover 2 serves to seal the rim of the first diaphragm 4 to the housing 1 and also forms a guide for the movable rigid body 3 and a seat for a return spring 8 as will appear from the following detail description of the parts.

The housing generally has the shape of an open bowl with a peripheral flange 1a extending in one plane about the bowl opening. The cover 2 in the preferred embodiment is shaped as a complementary open bowl with a peripheral flange 2a corresponding in size and orientation to flange 1a.

The movable rigid body 3 has the shape of a cylindrical bowl open towards housing 1 and having a plane peripheral flange 3a extending outwardly from the edge of the cylindrical bowl.

The first annular diaphragm 4 has an outer edge 4a sealingly inserted between housing and cover flanges 1a and 2a which are attached to each other by any convenient, conventional means (not shown) such as screwing. The inner edge 4b of the first annular diaphragm 4 is sealingly attached to the flange 3a of the rigid body 3, for example by sealing insertion between the outward face of this flange 3a and a corresponding flange 60a extending from a substantially bowl-shaped clamping and guiding element 60 placed over the bowl opening of the rigid body 3 and attached thereto at the complementary flanges 3a and 60a by any convenient, conventional means (not shown) such as screwing.

The outer edge 5a of the second annular diaphragm is also sealingly inserted between flanges 3a and 60a, it being understood that the inner edge 4b of the first diaphragm 4 may be integral with the outer edge 5a of the second diaphragm 5.

The inner edge 5b of annular diaphragm 5 is sealingly attached, such as by clamping, to the upper peripheral edge 9a of a body 9 integral with or rigidly attached to the inside of the bottom of the bowl constituting housing 1, said body 9 having a cross-sectional extension and shape permitting its penetration, with considerable play, into the bowl cavity of rigid body 3 in the FIG. 1 position thereof. Body 9 has a length such that its plane upper surface within peripheral edge 9a is approximately on the same level as the joint between housing and cover flanges 1a, 2a.

Ducts 10a and 10b extend through the wall of housing 1 into and longitudinally through body 9 and are terminated by ports 10a', 10b' opening in the end surface of body 9 within peripheral edge 9a.

It will be understood that the second diaphragm 5, rather than having the free edge of an inner aperture attached to edge 9a of body 9, may be designed without such inner aperture and be attached, eg clamped, to the entire top surface of body 9 within edge 9a in which case obviously perforations corresponding to ports 10a', 10b' will be provided in diaphragm 5.

By the parts so far described two chambers of importance for the operation of the pump are defined:

The pump chamber or air-suction chamber 24 has solid walls constituted by housing 1 including body 9 and by the flange portions 3a, 60a of rigid body 3 as well as flexible wall portions constituted by diaphragms 4 and 5. Outward communication of the pump chamber 24 comprises a tube 11 forming an inlet and a tube 12 forming an outlet.

The motor chamber 25 has solid walls constituted by the bowl portion of rigid body 3 and by the end surface of body 9 within the peripheral edge 9a, as well as flexible wall portions constituted by diaphragm 5. Driving gas under pressure is supplied to motor chamber 25 through duct 10a and port 10a' and exhausted through duct 10b and port 10b', gas supply and exhaust being controlled by a bistable valve assembly which can be designed in many ways according to already known technology. This valve arrangement, therefore, is only symbolically shown by parts 6, 7 in FIGS. 1 and 2, but two embodiments of this valve arrangement will be described in detail by reference to FIGS. 3 and 4. While the valve arrangements in FIGS. 1 and 2 is shown to be positioned within motor chanber 25, it could just as well be positioned outside the motor chamber 25 without this alteration having any appreciable effect on the scope of the invention.

Inlet duct 10a communicates with a pressure gas supply line 23 via a needle valve 29 permitting adjustment of the intake flow of the driving gas and consequently the operating frequency of the pump. A one-way valve 30 connects the driving gas inlet duct to the ambient atmosphere so that air is drawn into the motor chamber via this valve when the pump is being manually operated.

Figure 2:
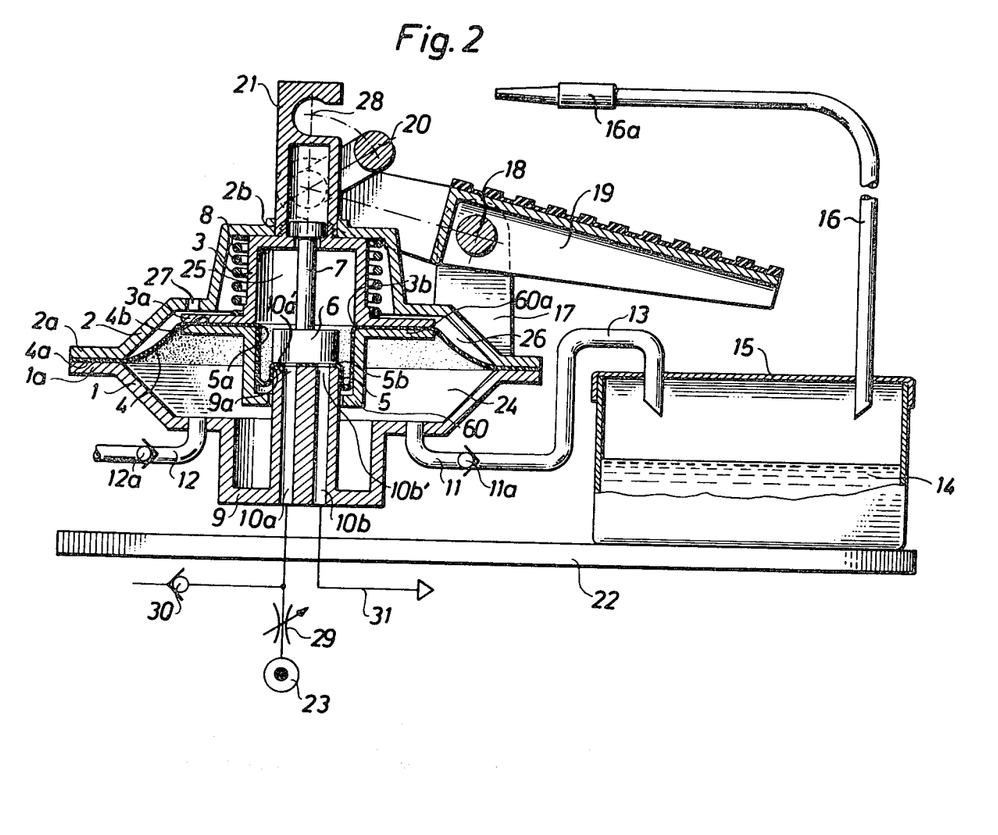
FIG. 2 is a schematic vertical cross-section of the pump with the movable motor member in top position.

Under the action of driving gas supplied to and exhausted from the motor chamber 25 under the control of valve unit 6, 7 the rigid body 3 with attached diaphragms 4 and 5 will reciprocate between the positions shown in respectively FIGS. 1 and 2. An element 21 acting as a pulling rod in connection with manual operation is attached, as by screwing to the outer bottom side of the bowl constituted be rigid body 3 and extends therefrom in the direction of reciprocation of rigid body 3 along the centre line of housing 1. The free outer end of the pulling rod 21 is slidingly guided in a corresponding bore 2b in the central portion of cover 2.

A coil spring 8 is inserted between flange 3a of rigid body 3 and the bottom of cover 2 to urge rigid body 3 towards the inoperative rest position shown in FIG. 1.

From a comparison between FIGS. 1 and 2 it will be evident that in the inoperative position of FIG. 1 both the pump chamber 24 and the motor chamber 25 have minimum volume whereas in the pressure-gas operative position of FIG. 2 both chambers have maximum volume.

A third chamber—without importance for the operation of the pump—is formed between the cavity of cover 2, the outer surface of rigid body 3 including flange 3a and diaphragm 4. This chamber is in open communication with the ambient atmosphere through a port 27 in cover 2. Obviously, cover 2 need not be a closed bowl but may be some kind of lattice construction supporting flange 2a and guiding pulling rod 21.

The tracheal suction pump further comprises a secretion reservoir 14 air-tightly closed by cover 15. One end of a suction tube 16 sealingly extends through cover 15 into reservoir 14 whereas the other end of suction tube 16 in the customary way is terminated by a suction tip 16a or suction catheter which may be introduced into the mouth and air ducts of the patient.

Pump chamber inlet tube 11 via a check valve 11a communicates with the tube 13 the free end of which sealingly extends through cover 15 into reservoir 14. Pump chamber outlet tube 12 via a check valve 12a communicates with the ambient atmosphere. Check-valves 11a and 12a prevent air from flowing respectively from suction chamber 24 into reservoir 14 and from the ambient atmosphere into the pump or air suction chamber 24.

Figure 3:
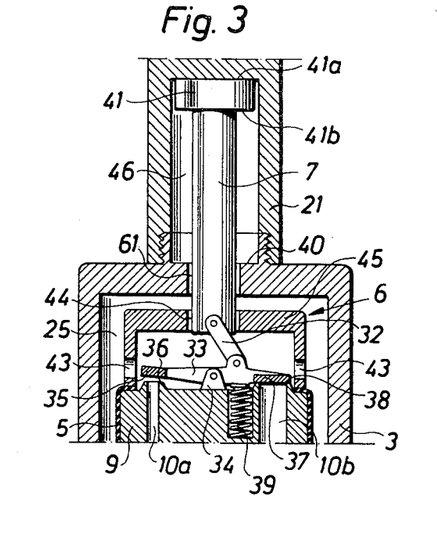
FIGS. 3 and 4 are schematic sectional views at an increased scale of respectively a first and a second, presently preferred, embodiment of valve means cooperating with the motor chamber of the pump.

In FIG. 3 there is shown an embodiment of a valve arrangement 6, 7 for cooperation with a motor chamber 25 of a tracheal suction pump of the type shown in FIGS. 1 and 2. In this case pulling rod 21 is hollow and closed at its outer free end and its cavity 46 communicates with motor chamber 25 within rigid body 3. As shown in FIG. 3 pulling rod 3 is designed as a cylindrical bowl sealingly—such as by screwing—attached to the outer bottom surface of rigid body 3 around a central aperture 47 establishing communication between the inner cavity of pulling rod 21 and the motor chamber 25.

A valve housing 6 is attached to the upper surface of body 9 which as previously described and illustrated in FIGS. 1 and 2 is integral with or rigidly attached to the inside of the bottom of the bowl constituting housing 1 and which has a cross-sectional extension and shape permitting its penetration into the bowl cavity within rigid body 3. It will be noted that in the FIG. 3 embodiment the inner edge of annular second diaphragm 5 is sealingly clamped between the upper surface of body 9 and the lower edge surface of valve housing 6. Communication between the interior of valve housing 6 and motor chamber 25 is established by the provision of at least one aperture 43 extending through a cylindrical wall portion of housing 6.

A shifting rod 7 is adapted to reciprocate in cavity 46 in pulling rod 21, said shifting rod 7 having a head 41 facing the bottom of cavity 46. In the position shown in FIG. 3 and roughly corresponding to the position of the parts illustrated in FIG. 1, outer surface 41a of head 41 is in contact with the bottom of cavity 46. Shifting rod 7 extends from the inner surface 41b of head 41 through aperture 61 and a corresponding aperture 44 in the bottom 45 of housing 6, the play between the wall defining aperture 44 and the outer surface of rod 7 as well as the play between the inner cylindrical wall of cavity 46 and the outer cylindrical wall of head 41 being so chosen that shifting rod 7 is securely but not sealingly guided during its reciprocating movement. It will be noted that the diameter of aperture 61 in the bottom wall of rigid body 3 is chosen so that head 41 in the lower most position of shifting rod 7 will abut against the outer surface zone 40 of the bottom of body 3 surrounding aperture 61.

Pressure gas supply duct 10a opens into the valve housing 6 at a valve seat 36 adapted to be closed and opened by a first valve element 35. Driving gas exhaust duct 10b opens into valve housing 6 at a valve seat 38 adapted to be opened and closed by a second valve element 37. It will be noted that driving gas exhaust duct 10b, valve seat 38 and valve have a larger diameter than driving gas supply duct 10a, its valve seat 36 and the first valve element 35. The first and second valve elements 35 and 37 respectively are attached to the ends of a valve rocker arm 33 journalled in a bearing 34 centrally attached to the free end surface of body 9. A link 32, pivotally attached to the lower end of shifting rod 7 and to valve rocker arm 33 intermediate the second valve element 37 and the bearing 34, acts to close exhaust valve element 37 against its seat 38 and to open supply valve element 35 from its seat 36 when rod 7 is depressed and, inversely, to open exhaust valve element 37 from its seat 38 and to close supply valve element 35 onto its seat 36 when rod 7 is pulled in an upward direction.

A coil spring 39 inserted into a bore in the upper surface of body 9 is in contact with the lower surface of valve rocker arm 33 in a position between the bearing 34 and the exhaust valve comprising valve element 37 and seat 38.

FIG. 3 shows the valve in its position when the movable rigid body 3 is in its lower most position as in FIG. 1. Shifting rod 7 is depressed by contact between its head surface 41a and the bottom of cavity 46, the supply valve composed of the valve element 35 and valve seat 36 is open, the exhaust valve 37, 38 is closed and coil spring 39 is tensioned. In this situation driving gas under pressure enters the motor chamber 25 and creates a pressure causing the movable rigid body 3 to move in an upward direction as seen in FIGS. 1-3. Shifting rod head 41 is now no longer restrained by the bottom of cavity 46, but exhaust valve seat 38 has such a size that the driving pressure in the motor chamber 25 will hold the valve rocker arm 33 in the position as shown against the force exerted by tensioned spring 39. When rigid body 3 is about to reach its uppermost position the lower most surface 41b of head 41 will engage the outer bottom surface 40 of rigid body 3 and shifting rod 7 will be lifted during the final movement of rigid body 3. Link 32 will exert a pulling action on valve rocker arm 33 lifting valve element 37 from its seat 38. Thereby the driving pressure prevailing in motor chamber 25 will be released enabling spring 39 to overcome the counteracting pressure force and to shift over valve rocker arm 33 to the position in which valve element 35 closes valve seat 36. Supply of driving pressure gas is thereby interrupted and rigid body 3 will be urged in a downward direction by return spring 8 (FIGS. 1 and 2) while driving gas is exhausted from motor chamber 25 via exhaust valve 37, 38 and duct 10b.

The starting position of the next cycle of reciprocation and valve operation is reached as soon as surface 41a of head 7 contacts the bottom of the cavity 46 within pulling rod 21, causing link 32 to depress rocker arm 33 to close exhaust valve 37, 38 and to open supply valve 35, 36.

By reference to FIG. 4 a preferred embodiment of the valve arrangement 6, 7 will now be described, it being understood that parts functionally corresponding to parts described in connection with the embodiment of FIG. 3 have the same reference designations as in the previous Figures even if they are shown in a slightly modified configuration.

Figure 4:
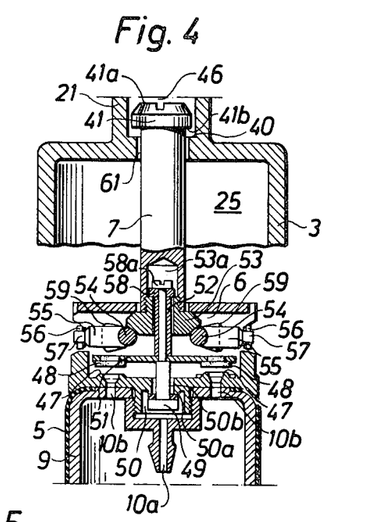

Also in the FIG. 4 embodiment the two main components of the valve arrangement are a valve housing 6 and a shifting rod 7. As in the previously described embodiment the shifting rod 7 has a head 41 with an upper surface 41a and a lower surface 41b, said head being reciprocatable in a cavity 46 provided in a hollow part 21 constituting a pulling rod and attached to rigid body 3 in such a way that the cavity 46 is communication with motor chamber 25 within rigid body 3.

Also in this embodiment the stroke length of shifting rod 7 is determined by abutment of upper head surface 41a against the bottom of cavity 46 and abutment of the lower head surface 41b against the outer bottom surface of rigid body 3 in zone 40 surrounding bore 61 in said bottom surface through which shifting rod 7 is reciprocating.

Also in this embodiment housing 6 is firmly attached by any convenient, conventional means, such as screws, to the upper end surface of body 9 which is integral with or rigidly attached to the inside of the bottom of the bowl constituting housing 1. As in the previously described embodiment diaphragm 5 is sealingly clamped between the lower surface of housing 6 and the upper surface of body 9.

Contrary to the previously described embodiment, body 9 is hollow and its cavity, in a way not shown, is in communication with pressure gas exhaust means. Pressure gas supply duct 10a extends through a connecting nipple disposed centrally within the cavity of body 9 and permitting a pressure gas supply tube or hose to be attached.

Duct 10a opens into a valve chamber 50 having a valve seat 50a opposite the end of duct 10a. A valve element 49 is movable within valve chamber 50 between valve opening and closing positions.

The two pressure gas exhaust ports 10b are respectively opened and closed by means of valve elements 48 cooperating with valve seats 47 each surrounding one of ports 10b. Valve elements 48 are supported for translatory movement towards and away from seats 47 on a common yoke 51 which is symmetrically attached to a guide element 52, the lower free end of which (seen as in FIG. 4) extends through a bore 50b connecting valve chamber 50 with the hollow interior of housing 6 and carries valve element 49 within valve chamber 50.

While shifting rod or valve rod 7 at its upper end is guided by its head 41 within cavity 46 and by its main body within bore 61 it is guided at its lower end in bore 44 in the upper surface of valve housing 6. Attached to the lower end of valve rod 7 is a cam body 53 extending into and closing a cavity 53a in the terminal end of valve rod 7.

Guide element 52 at its upper end opposite valve element 49 extends through a central bore 53b in cam body 53 with a loose fit into cavity 53a. A washer 58 of a diameter greater than the diameter of bore 53b is transversely fixed to the end of guide element 52 by means such as a screw 58a. In the position of the parts shown in FIG. 4 the washer 58 rests on the upper terminal end of cam body 53 within cavity 53a.

Considering housing 6 as stationary it will be understood that to the extent the position of rigid body 3 permits, the assembly formed by valve rod 7 and cam body 53 is longitudinally shiftable in relation to housing 6 and in relation to the assembly constituted by guide element 52, yoke 51 and valve elements 48 and 49, this latter assembly being longitudinally movable also in relation to the housing 6.

Two rollers 54 are urged against two opposed pairs of diverging cam surfaces on cam body 53 by means of thrust bodies 55 under the action of leaf springs 56 supported by studs 57. Each of the rollers 54 is guided in a triangular recess 59 provided in the valve housing 6.

In the position of the valve arrangement as shown in FIG. 4 the rigid body 3 is in its uppermost position and surface portion 40 around bore 61, by interaction with the lower surface 41b of head 41, has lifted valve rod 7 to such an extent that the rollers 54 have been moved past the cam top points. Under the action of springs 56 the rollers have moved inwardly towards each other forcing cam body 53 and thereby shifting rod 7 to move in an upward direction until the cam body 53 has come into contact with the inner surface of the upper wall of housing 6. At the same time the lower surface 41b of the head 41 of valve rod 7 is lifted above surface 40 on the outside of the bottom of rigid body 3 around bore 61.

Under the final portion of the movement of valve rod 7 cam body 53 engages washer 58 thereby lifting the guide element 52 to a position in which valve element 49 closes seat 50a while valve elements 48 are moved to a position above seats 47 thus opening outlet ports 10b. Interruption of the supply of driving gas under pressure through valve 49, 50 as well as release of pressure from the interior of motor chamber 3 via ports 10b causes the rigid body 3 to return from the position shown in FIG. 4 under the action of the return spring 8 (shown in FIGS. 1 and 2). When rigid body 3 is approaching its lowermost position (analogous to the position shown in FIG. 3) surface 41a is contacted by the bottom of cavity 46 causing the oblique cam surfaces in contact with rollers 54 to urge the rollers in an outward direction until the top points on both sides of the cam body have moved past the rollers which then are urged by springs 56 in an inward direction thereby moving cam body 53 downwardly towards yoke 51 forcing the yoke to move downwardly to a position in contact with seats 47 thereby closing exhaust ports 10b. Due to its connection to yoke 51 guide element 52 also will move down causing valve element 49 to leave seat 50a and thereby to admit renewed supply of driving gas under pressure from supply duct 10a. The rigid body 3 will now be moved again to the position shown in FIG. 4 and the reciprocating and valve operating cycle described before will be repeated.

It should be noted that the triangular recesses 59 in the valve housing 6 serve to improve the power transfer angle between the cam body 53 and the rollers 54 when the cam body moves the rollers or the rollers move the cam body because the rollers will move inwardly and outwardly along the inclined surfaces of the triangular recesses 59.

To a great extent the operation of the tracheal suction pump basically shown in FIGS. 1 and 2 and provided with a valve arrangement of any suitable type, such as either of the valve arrangements described above by reference to FIGS. 3 and 4, will be clear from the preceding description and accordingly only a brief recapitulation will be sufficient.

Due to the return spring 8 the rigid body 3 will always be in bottom position as shown in FIGS. 1 and 3 when the operation is started. The shifting rod 7 is thus depressed whereby the valve arrangement causes the inlet port 10a to be open and the exhaust port 10b to be closed. If compressed driving gas is then supplied through gas supply line 23, the gas will flow into the motor chamber 25 causing the rigid body 3 to rise. This increases the volume of pump chamber 24 and air is sucked-in through suction tube 16, the secretion reservoir 14, tube 13 and the checkvalve 11a. Suction continues until the rigid body 3 reaches its top position as shown in FIG. 2 where shifting rod 7 is pulled up so that the valve arrangement closes the inlet port 10a and opens the exhaust port 10b. Subsequently, the return spring 8 presses the rigid body 3 downwardly thereby exhausting the driving gas from the motor chamber 25 and simultaneously causing air aspired into the pump chamber 24 to be exhausted via checkvalve 12a. The return movement is completed by a renewed depression of shifting rod 7 and a return of the various valve elements to a position in which inlet port 10a is open and exhaust port 10b is closed.

The needle valve 29 regulates the intake flow of the driving gas and consequently the operating frequency of the pump.

When the pump is idling, ie when there is intake of air merely via suction tube 16, the pump will operate at a constant frequency. However, if the suction tube 16 is closed-up, the pump will stop working after a few strokes because the maximum vacuum then has been established in the secretion reservoir 14 and the pump chamber 24. A balance is achieved between the forces acting upon the rigid body 3, ie the driving gas pressure acting on the wall of the motor chamber and the vacuum acting on the wall of the pump chamber, the resilient force of the return spring 8. Thus, the consumption of driving gas ceases although maximum suction is maintained in the suction tube 16. In practice this operating characteristic is highly advantageous because when removing secretion from the mouth and air ducts of the patient a high air speed is desirable at the suction tip 16a in order to collect as much as possible of the secretion not in the immediate vicinity of the suction tip. However, when the secretion is in contact with the suction tube it is necessary that the pump immediately builds up a maximum vacuum with as small a consumption of driving gas as possible.

In addition to the economical use of driving gas thus obtained, there is the further advantage that the operator, by being able to see and hear the operation mode of the pump, has a clear impression of the effectiveness of the suction.

The driving gas is normally supplied by a high pressure cylinder with pressure regulating valve; the pressure can be regulated to adjust the maximum vacuum of the pump as convenient.

Figure 5:
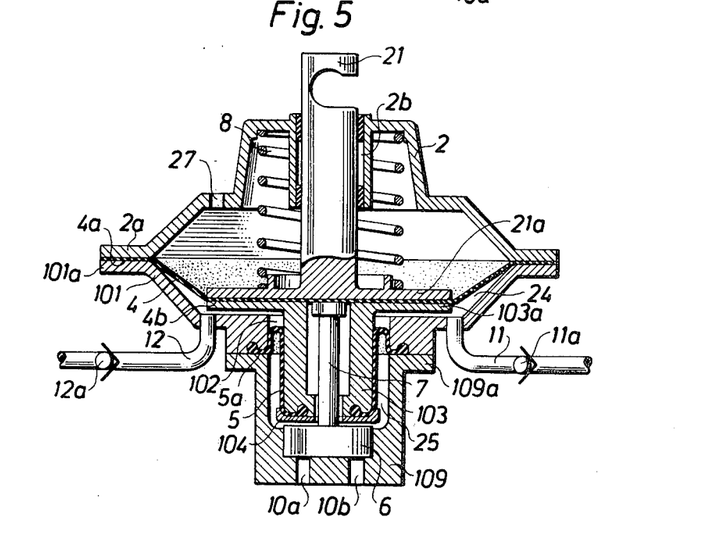
FIG. 5 is a schematic cross-section corresponding to the pump assembly portion of FIG. 1 and showing a modification of the housing and motor chamber of the pump.

In so far as the embodiment according to FIG. 5 of the pump assembly is in agreement with the embodiment shown in FIGS. 1 and 2 the same reference numerals are used. According to FIG. 5 the pump assembly comprises a stationary housing 101 which together with wall portions of a movable rigid body 103, a first annular flexible diaphragm 4 and a second annular flexible diaphragm 5 defines a central motor chamber 25 and a concentric pump chamber 24. Both diaphragms 4 and 5 are conveniently made of rubber. While the first diaphragm 4 is of the tapered type the second diaphragm 5 is of the rolling type. A cover 2 serves to seal the rim of the first diaphragm 4 to the housing 1 and also forms a guide for the movable rigid body 103 and a seat for a return spring 8 as will appear from the following detail description of the parts.

The housing 101 generally has the shape of an open bowl having a central hole 102 in the bottom, said hole 102 having a cross-sectional extension and shape permitting the penetration, with considerable play of the rigid body 103 as will be explained later.

A housing element 109 in the shape of a substantially cylindrical bowl with an outer flange 109a around the open end is attached by conventional means, such as screwing, to the outer bottom surface of the bowl-shaped housing 101 so that the bowl cavity of housing element 103 forms an extension of the hole 102 in the bottom of housing 101.

The movable rigid body 103 has the shape of a cylindrical bowl the outer bottom surface of which faces the bottom of the cylindrical bowl cavity in housing element 109. A plane peripheral flange 103a extends outwardly from the edge of cylindrical bowl 103.

The first annular diaphragm 4 has an outer 4a sealingly inserted between housing and cover flanges 101a and 2a which are attached to each other by any convenient, conventional means, not shown, such as screwing. The inner edge 4b of the first annular diaphragm 4 is sealingly attached to flange 103a of the rigid body 103, for example, by sealing insertion between the outer face of this flange 3a and a corresponding flange 21a extending from the inner end of an element 21 acting as a pulling rod in connection with manual operation. Flanges 103a and 21a are attached to each other by any convenient, conventional means, not shown, such as screwing.

In the same way as in the embodiment according to FIGS. 1 and 2 pulling rod 21 extends from its ends connected to rigid body 103 in the direction of reciprocation of rigid body 103 along the centerline of housing 1. Also in the FIG. 5 embodiment the free outer end of the pulling rod 21 is slidingly guided in a corresponding bore 2b in the central portion of cover 2.

Spring 8 is in this case inserted between the bottom of cover bowl 2 and the opposed side of flange 21a extending from the inner end of pulling rod 21.

The outer edge 5a of the second annular diaphragm is sealingly inserted between the outer bottom portions of housing 101 surrounding hole 102 and the outer surface of flange 109a of housing portion 109. The inner edge 5b of the second annular diaphragm 5 is sealingly attached, such as by clamping between the bottom surface of rigid body 103 and a clamping element 104 attached to the bottom face of rigid body 109 by any convenient, conventional means, not shown, such as screwing.

Rigid body 103 has a cross-sectional extension and shape permitting its penetration with considerable play into the bowl cavity formed in housing 101 and housing portion 109 in the position of the parts illustrated in FIG. 5.

In the same way as in the embodiment according to FIGS. 1 and 2 ducts 10a and 10b extend through the bottom wall of housing portion 109 into communication with the motor chamber 25 formed within hole 102 in housing portion 101, the adjacent bowl cavity in housing portion 109, and the interior of body 103.

By the parts so far described by reference to FIG. 5 two chambers of importance for the operation of the pump are defined: The pump chamber or air-suction chamber 24 has solid walls constituted by housing 101 and rigid body 103 together with its flange 103a as well as flexible wall portions constituted by diaphragms 4 and 5. As in the embodiment according to FIGS. 1 and 2 outward communication of the pump chamber 24 comprises a tube 11 forming an inlet and a tube 12 forming an outlet, these tubes having checkvalves 11a and 12a respectively acting as previously described.

The motor chamber 25 has solid walls defined by the inner walls of the bowl within rigid body 103 and by the inner walls of the bowl within housing portion 109 as well as flexible wall portions constituted by diaphragm 5. Driving gas supply and exhaust as well as the fundamental construction of valve arrangement 6, 7 exactly corresponds to the embodiment of FIGS. 1 and 2.

A very definite advantage of the tracheal suction pump construction according to the present invention is its ability to be manually operated, for example in a case where driving gas is not available. In this case pulling rod 21 which, as described before, serves as guiding member of rigid body 3, 103, at its free end is coupled to a cantilever pedal 19 journaled on a pivot pin 18 held by a bracket 17 which in turn is rigidly attached to cover 2 by any convenient means such as screwing or welding. As shown in FIGS. 1, 2, 5 and 6, the free outer end of pulling rod 21 is provided with a slotted eye 28 forming a pivot bearing for a crank 20 laterally extending from cantilever pedal 19.

Figure 6:
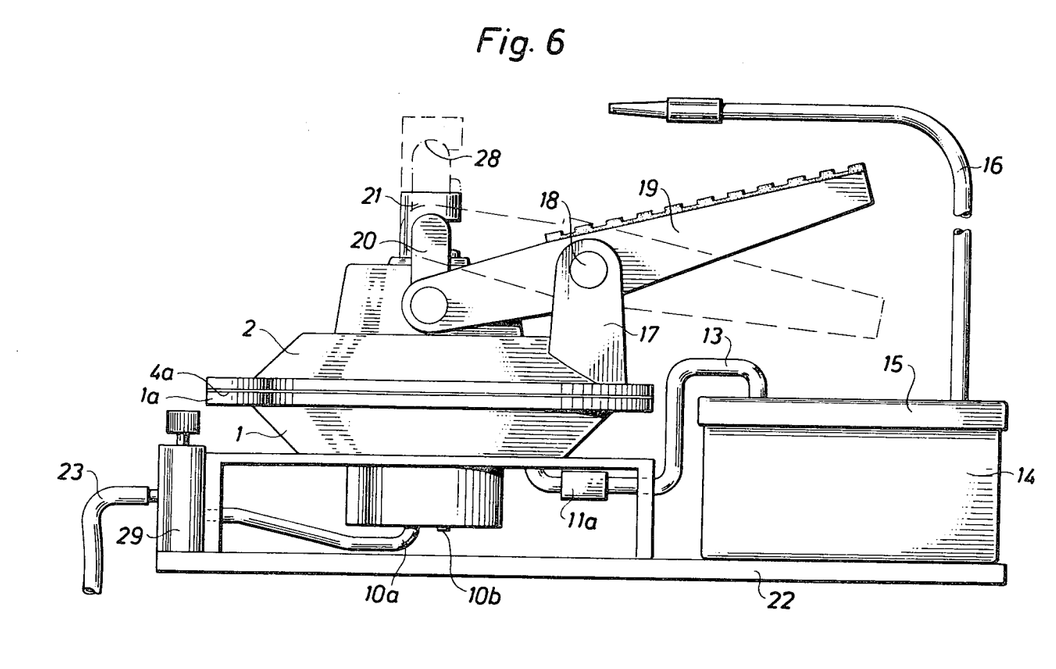
FIG. 6 is a side view corresponding to FIGS. 1 and 2 of the pump with the cantilever pedal connected for manual operation.

If manual operation of the tracheal suction pump is required, the gas supply is discontinued and the crank 20 is attached to the slotted eye 28 of the pulling rod 21 by a swinging movement as illustrated in FIG. 2. By working the pedal 19 up and down as shown in FIG. 6 the same result is achieved as previously described in connection with automatic operation. In this case only air is sucked into the motor chamber 24 via the one-way valve 30 during the suction stroke and this air is exhausted again through duct 10b during the return stroke.

A still better understanding of the invention may be derived from the following explanation regarding an example of the design of a tracheal suction pump incorporating the teachings of the invention.

EXAMPLE OF DESIGN

As it is desirable that the pump can be easily operated manually, and that the pump should simultaneously be as compact as possible, it is expedient that the pump's stroke volume is proportioned so that the nominal operating frequency during idling can be limited to 120–140 strokes per minute. The stroke volume of the pump chamber should be approximately 200 ml in order to obtain a sufficient air flow at the suction nozzle with this pump frequency.

The driving gas will normally always be available at a regulated pressure of at least 3 kp/cm$^2$ and maximum 5 kp/cm$^2$. A tracheal suction pump's normal vacuum yield with blocked suction tubing 16 is usually stated as minimum −0.4 kp/cm$^2$.

When the ratio between the area of the common movable rigid body 3 forming the motor chamber 25 and the ring area forming the pump chamber's 24 movable wall corresponds to the ratio between the vacuum −0.4 kp/cm$^2$ and the minimum pressure of the driving gas, 3 kp/cm$^2$, then the movable rigid body 3 will be in balance, apart from the return spring's force. This should be as small as possible to ensure that the consumption of driving gas is kept as economical as possible. It turns out, however, that approximately 0.5 kp/cm$^2$ of the driving gas pressure must be regarded as necessary to compress the return spring. The area ratio, therefore, must be approximately $(0.4)/(3-0.5)=0.16$ If the pump chamber's ultimate effective diameter is notated as DP and the motor chamber's as DM, the following results:

$$\frac{\frac{\pi}{4} \times DM^2}{\frac{\pi}{4}(DP^2 - DM^2)} = \frac{1}{\left(\frac{DP}{DM}\right)^2 - 1} = \text{approx. } 0.16$$

$$\text{or } \frac{DP}{DM} = \sqrt{\frac{1}{0.16} + 1} = \text{approx. } 2.7$$

In possession of this information, a specialist in the field will be able to construct a suction pump according to the invention.

What I claim is:

1. A suction pump comprising a pump assembly having a suction chamber of variable volume with an outlet leading to the ambient atmosphere and an inlet communicating with a secretion-receiving reservoir with attached tubing permitting suction of secretion, primarily from the air ducts of an unconscious patient, said pump being characterized by the pump assembly comprising a housing enclosing the suction chamber and closed at one end by means comprising a first annular diaphragm forming a boundary between the suction chamber and the atmosphere, and a rigid body centrally sealingly attached to said first annular diaphragm and guided by means connected to said housing for movement relative to the housing and having wall portions defining, together with means forming part of the housing, a motor chamber of variable volume delimited from said suction chamber by a second annular diaphragm, said motor chamber communicating with driving gas supply and exhaust connections and a valve arrangement for the intake and exhaust of compressed driving gas.

2. The suction pump as claimed in claim 1, further characterized in that said valve arrangement is provided within the motor chamber and that driving gas supply and exhaust connections communicate with the valve arrangement through the means forming part of the housing.

3. The suction pump as claimed in claim 1, further characterized by said means guiding the rigid body being a structure having a peripheral edge attached to a peripheral edge of the housing at said one end thereof with the peripheral edge of the first diaphragm sealingly interposed between said peripheral edges of the structure and housing.

4. The suction pump as claimed in claim 1, further characterized in that the guiding means and housing define a path of movement of the rigid body between positions in which the motor chamber and the suction chamber simultaneously have respectively maximum and minimum internal volumes.

5. The suction pump as claimed in claim 4, further characterized in that means integral with the housing extend into the path of movement of the rigid body to increasingly restrict the internal volume of the motor chamber during movement of the rigid body from its end position of maximum internal volume to its end position of minimum internal volume.

6. The suction pump as claimed in claim 4, further characterized by spring means urging the rigid body towards a rest position coinciding with the end position in which the motor chamber has minimum internal volume.

7. The suction pump as claimed in claim 1, further characterized by the provision of a pulling rod connected to the rigid body and outwardly extending through the means guiding the rigid body to enable the rigid body to be moved manually for operation of the pump.

8. The suction pump as claimed in claim 7, further characterized by a cantilever pedal swingable about a pivot in fixed spatial relation to the pump housing and having a longer actuating arm and a shorter operating arm, a link hingedly connected to the free end of the operating arm, and means provided on the outwardly extending end of the pulling rod and adapted temporarily to receive and hingedly hold a portion of the link to enable the pulling rod and rigid body to be moved by swinging actuation of the pedal about its pivot.

9. The suction pump as claimed in claim 1, characterized in that said valve arrangement comprises first valve means cooperating with first seating means and second valve means cooperating with second seating means, movable means alternatively supporting said first and second valve means in such a way that one of said valve means is in closing contact with its seating means when the other one of said valve means is out of closing contact with its seating means, said movable means being connected to a valve-shifting element movable in cooperative relationship with the rigid body and having wall portions contacted by wall portions of the rigid body in each end portion of its movement to shift the valve-shifting element and thereby the movable valve suporting means to positions causing the valve means to respectively supply and exhaust driving gas for reversal of the movement of the rigid body.

10. The suction pump as claimed in claim 1, further characterized in that the first annular diaphragm has an inner circumference and an outer circumference, and the second annular diaphragm is disposed within the inner circumference of the first annular diaphragm.

11. A suction pump comprising:
   I. means comprising flexible portions and defining an air-suction chamber,
   II. movable motor means connected to the flexible portions to move them, during a suction stroke, to a position in which the inner volume of the air-suction chamber is increased and, during an exhaust stroke, to a position in which the inner volume of the air-suction chamber is reduced,
   III. means firmly connected to the means defining the air-suction chamber and adapted to guide the motor means for reciprocating movement towards and away from the air-suction chamber,
   IV. a secretion-receiving reservoir having an inlet adapted suctionally to receive air and secretion from the air-ducts of a patient, and an outlet,
   V. a suction chamber outlet communicating with the ambient atmosphere,
   VI. a suction chamber inlet communicating with the reservoir outlet,
   VII. check-valve means in the air-suction chamber inlet and outlet acting to prevent air from flowing respectively from the ambient atmosphere into the suction chamber and from the suction chamber into the reservoir, said means defining an air-suction chamber comprising:
(1) a rigid housing having an open end delimited by a peripheral rim, and
(2) means closing said open end, said means comprising:
   (a) a first annular diaphragm constituting one of the flexible portions of the means defining the air-suction chamber and having an outer edge sealingly attached to the peripheral rim, and an inner edge,
   (b) a rigid hollow body constituting the motor means and having wall portions defining, together with means forming part of the housing, a motor chamber oen at one end along an edge facing the air-suction chamber, and flange means sealingly attached to the inner edge of the first annular diaphragm,
   (c) a second annular diaphragm constituting another one of the flexible portions defining the air-suction chamber and having an outer edge sealingly attached to the edge of the open end of the motor chamber, and an inner edge,
   (d) a wall portion of the housing opposite the open end of the motor chamber having a circumferential edge zone in sealing contact with the inner edge of the second annular diaphragm, gas supply and exhaust ducts extending through said wall portion to form gas supply and exhaust ports within the circumferential edge zone and attachable at the outer end to outer gas supply and exhaust connections, valve means being provided, said valve means being alternatively movable by the movable motor means between gas supply and exhaust duct closing and opening positions.

12. A suction pump comprising:
I. means comprising flexible portions and defining an air-suction chamber,
II. movable motor means connected to the flexible portions to move them, during a suction stroke, to a position in which the inner volume of the air-suction chamber is increased and, during an exhaust stroke, to a position in which the inner volume of the air-suction chamber is reduced,
III. means firmly connected to the means defining the air-suction chamber and adapted to guide the motor means for reciprocating movement towards and away from the air-suction chamber,
IV. a secretion-receiving reservoir having an inlet adapted suctionally to receive air and secretion from the air-ducts of a patient, and an outlet,
V. a suction chamber outlet communicating with the ambient atmosphere,
VI. a suction chamber inlet communicating with the reservoir outlet,
VII. check-valve means in the air-suction chamber inlet and outlet acting to prevent air from flowing respectively from the ambient atmosphere into the suction chamber and from the suction chamber into the reservoir, said means defining an air-suction chamber comprising:
(1) a rigid housing having an opend end delimited by a peripheral rim, and
(2) means closing said open end, said means comprising:
   (a) a first annular diaphragm constituting one of the flexible portions of the means defining the air-suction chamber and having an outer edge sealingly attached to the peripheral rim, and an inner edge,
   (b) a rigid hollow body constituting the motor means and having wall portions defining, together with means forming part of the housing, a motor chamber open at one end along an edge facing the air-suction chamber, and flange means sealingly attached to the inner edge of the first annular diaphragm,
   (c) a second annular diaphragm constituting another one of the flexible portions defining the air-suction chamber and having an inner edge sealingly attached to the edge of the open end of the motor chamber, and an outer edge,
   (d) a wall portion of the housing opposite the open end of the motor chamber having a circumferential edge zone in sealing contact with the outer edge of the second annular diaphragm, gas supply and exhaust ducts extending through said wall portion to form gas supply and exhaust ports within the circumferential edge zone and attachable at the outer end to outer gas supply and exhaust connections, valve means being provided, said valve means being alternatively movable by the movable motor means between gas supply and exhaust duct closing and opening positions.

* * * * *